United States Patent [19]

Ginns et al.

[11] Patent Number: 6,074,864
[45] Date of Patent: *Jun. 13, 2000

[54] CLONED DNA FOR SYNTHESIZING UNIQUE GLUCOCEREBROSIDASE

[75] Inventors: Edward I. Ginns; Brian Martin, both of Bethesda; Kara A. Maysak, Chevy Chase, all of Md.; William K. Eliason, Reston, Va.; Mary E. LaMarca, Bethesda, Md.

[73] Assignee: The United States of America as represented by the Department of Health and Human Services, Washington, D.C.

[*] Notice: This patent is subject to a terminal disclaimer.

[21] Appl. No.: 08/186,256

[22] Filed: Jan. 13, 1994

Related U.S. Application Data

[63] Continuation of application No. 07/925,333, Aug. 6, 1992, abandoned, which is a continuation of application No. 07/474,307, Feb. 5, 1990, abandoned, which is a continuation of application No. 07/137,796, Dec. 23, 1987, abandoned.

[51] Int. Cl.$^7$ .............................. C12N 9/42; C12N 5/10; C12N 15/63; C12N 15/86
[52] U.S. Cl. .................. 435/209; 435/240.2; 435/320.1; 530/350
[58] Field of Search .............................. 435/69.1, 172.1, 435/172.3, 320.1, 240.2, 209; 536/23.1, 23.2, 23.5; 530/350

[56] References Cited

U.S. PATENT DOCUMENTS 4,745,051   5/1988   Smith et al. ........................ 435/69.51

OTHER PUBLICATIONS

Retrovirus–mediated Transfer of the Human Glucocerebrosidase Gene to Gaucher Fibroblasts—Prabhakara V. et al.—Mol. Biol. Med. (1986) 3, 293–299.
Acid –Glucosidase: Enzymology and Molecular Biology of Gaucher Disease Gregory A. Grabowski et al.,—Biochemistry and Molecular Biology, vol. 25(6), 1990, pp. 385–414.
A mUtation In The Human Glucocerebrosidase Gene In Neuronopathic Gaucher's Disease—Tsuji et al.,—New England Journal of Med. 316:570–575 Mar. 5, 1987.
Genetic Heterogeneity In Type 1 Gacher Disease: Multiple genetypes in Ashkenazic and Non–Ashkenazic individuals Tsuji et al.,—Proc. Natl. Acad. Sci. USA, vol. 85, pp. 2349–2352, Apr. 1988 Medical Sciences.
Choudary, et al., "The Molecular Biology of Gaucher Disease and the Potential for Gene Therapy" Cold Spring Harbor Lab. 1986.
Dinur, et al., *Proc. Natl. Acad. Sci. USA* 8383:1660–1664, 1986.
Sorge, et al. *Proc. Natl. Acad. Sci. USA* 82:7289–7293, 1985.
Tsuji, et al., *The Journal of Biological Chemistry* 261:50–53, 1986.
Takasaki, et al. *The Journal of Biological Chemistry* 259:1011–10117 1984.
Furbish, et al. *Proc. Natl. Acad. Sci. USA* 74:3560–3563, 1977.
Basu, et al., *The Journal of Biological Chemistry* 259:1714–1719 1984.
Erickson, et al., *The Journal of Biological Chemistry* 260:14319–14324 1985.
Choudray, et al., *Mol. Biol. Med.* 3:293–299, 1986.
Sorge, et al., *Proc. Natl. Acad. Sci. USA* 84:906–909, 1987.
Sorge, et al., *Proc. Natl. Acad. Sci. USA* 82:5442–5445, 1985.
Beutler, et al., *Proc. Natl. Acad. Sci. USA* 83:7472–7474, 1987.
Grabowski, et al. *Am. J. Hum. Genetics* 499–510, 1985.
Ginns et al. (1984), Biochem. Biophys. Res. Com., vol. 123, pp. 574–580.
Reiner et al. (1987), DNA, vol. 6, pp. 101–108.
Brady et al. (1980), Birth Defects: Original Article Series, vol. XVI, pp. 361–368.
Smith et al., Mol. and Cell. Biol., 1983, vol. 3, No. 12, pp. 2160–2165.
Zuckow et al., Bio/Technology, 1988, vol. 6, pp. 47–55.
Cameron et al., TIBTECH, Mar., 1989, vol. 7, pp. 66–70.
Lebacq–Verhezden et al., Mol. and Cell. Biol., Aug. 1988, vol. 8, pp. 3129–3135.

*Primary Examiner*—David Guzo
*Attorney, Agent, or Firm*—Foley & Lardner

[57] ABSTRACT

Glucocerebrosidase produced by recombinant methods and having use for treatment of Gaucher's disease is disclosed. A cDNA for encoding the specific protein is taught along with the method of preparing the construct used to produce the protein.

15 Claims, 7 Drawing Sheets

FIG. 1-A

```
                                                                                                    46
     G GAG TTT TCA AGT CCT TCC AGA GAG GAA TGT CCC AAG CCT TTG AGT
 47

12
         Ala Val Ser Trp Ala Met Ala Gly Ser Leu Thr Gly Leu Leu Leu Gln                             94
     AGG GTA AGC ATC TGG GCA ATG GCT GGC AGC CTC ACA GGA TTG CTA CTT CAG
 13
 95

Gly Tyr Ser Ser Val Val Cys Val Cys Val Cys Asn Ala Thr Tyr Lys Ser Phe                    28
     GGC TAC AGC AGC GTG GTG TGT GTC GTG TGC AAT GCC ACA TAC AAA AGC TTC                            142
 29
143

Phe Asp Pro Pro Thr Phe Pro Ala Leu Gly Thr Leu Leu Leu Ser Asp                            44
     TTT GAC CCC CCG ACC TTT CCT GCC CTT GGT ACC TTG CTA TAC GAC AGC                                190
 45
191

Ser Thr Arg Arg Gly Ser Gly Arg Met Glu Leu Ser Met Gly Arg Tyr Glu                        60
     AGT ACA CGC CGA AGT GGG CGA CGG ATG GAG AGT ATG GGG AGC CGC TAT GAG                            238
 61
239

Ala Asn His Thr Gly Thr Gly Gly Thr Leu Leu Phe Gly Thr Met Gln Ile Gln                    76
     GCT AAT CAC ACG GGC ACA GGC GGC ACC CTG CTA TTC GGG ACC ATC CAG                                286
 77
287

Lys Phe Gln Lys Val Lys Gly Phe Pro Gly Leu Glu Leu Leu Gln Glu Gln                        92
     AAG TTC CAG AAA GTG AAG GGA TTT GGA CTG GAG CTG CTG CAG GAA CAG                                334
 93
335

Ala Leu Asn Ile Leu Ala Leu Ser Pro Pro Ala Met Thr Asp Ala Ala                           108
     GCT CTC AAC ATC CTT GCC CTG TCA CCC CCT GCC ATG ACA GAT GCT GCT                                382
109
383

Lys Ser Tyr Phe Ser Glu Gly Ile Gly Tyr Asn Ile Leu Arg Val                               124
     AAA TCG TAC TTC TCT GAA GAA GGA ATC GGA TAT AAC ATC ATC CTA CTT                                430
125
431                                                                                                140
                                                                                                   478
```

FIG. 1-B

```
141  Pro Met Ala Ser Cys Asp Phe Ser Ile Arg Thr Tyr Thr Tyr Ala Asp  156
479  CCC ATG GCC AGC TGT GAC TTC TCC ATC CGC ACC TAT ACC TAT GCA GAC  526

157  Thr Pro Asp Phe Gln Leu His Asn Phe Arg Thr Ser Leu Pro Glu Asp  172
527  ACC CCT GAT TTC CAG TTG CAC AAC TTC CGA ACC AGC CTC CCA GAG GAT  574

173  Thr Lys Leu Lys Ile Pro Leu Ile His Arg Ala Leu Gln Leu Ala Gln  188
575  ACC AAG CTC AAG ATA CCC CTG ATT CAC CGA GCC CTG CAG TTG GCC CAG  622

189  Arg Pro Val Ser Leu Leu Ala Ser Pro Thr Ser Pro Thr Trp Leu     204
623  CGT CCC GTT TCA CTC CTT GCG GCC AGC CCC ACA TCA CCC ACT TGG CTC  670

205  Lys Thr Asn Gly Ala Val Asn Gly Lys Gly Ser Leu Lys Phe Leu     220
671  AAG ACC AAT GGA GCG GTG AAT GGG AAG GGG TCA CTC AAG TTC CTC      718

221  Gly Asp Ile Tyr His Gln Thr Trp Ala Arg Tyr Phe Val Lys Phe Leu  236
719  GGA GAC ATC TAC CAC CAG ACC TGG GCC AGA TAC TTT GTG AAG TTC CTG  766

237  Asp Ala Tyr Ala Glu His Lys Leu Gln Phe Trp Ala Val Thr Ala Glu  252
767  GAT GCC TAT GCT GAG CAC AAG TTA CAG TTC TGG GCA GTG ACA GCT GAA  814

253  Asn Glu Pro Ser Ala Gly Leu Leu Ser Gly Tyr Pro Phe Gln Cys Leu  268
815  AAT GAG CCT TCT GCT GGG CTG TTA AGT GGA TAC CCC TTC CAG TGC CTG  862

269  Gly Phe Thr Pro Glu His Gln Arg Asp Phe Ile Ala Arg Asp Leu Gly  284
863  GGC TTC ACC CCT GAA CAT CAG CGA GAC TTC ATT GCC CGT GAC CTA GGT  910

285  Pro Thr Leu Ala Asn Ser Thr His His Asn Val Arg Leu Leu Met Leu  300
911  CCT ACC CTC GCC AAC AGT ACT CAC CAC AAT GTC CGC CTA CTC ATG CTG  958
```

| | | | | | | | | | | | | | | | | |
|---|---|---|---|---|---|---|---|---|---|---|---|---|---|---|---|---|
| 301 | Asp | Asp | Gln | Arg | Leu | Leu | Leu | Pro | His | Trp | Ala | Lys | Val | Val | Leu | Thr | 316 |
| 959 | GAT | GAC | CAA | CGC | TTG | CTG | CTG | CCC | CAC | TGG | GCA | AAG | GTG | GTA | CTG | ACA | 1006 |
| 317 | Asp | Pro | Glu | Ala | Ala | Lys | Tyr | Val | His | Gly | Ile | Ala | Val | His | Trp | Tyr | 332 |
| 1007 | GAC | CCA | GAA | GCA | GCT | AAA | TAT | GTT | CAT | GGC | ATT | GCT | GTA | CAT | TGG | TAC | 1054 |
| 333 | Leu | Asp | Phe | Leu | Ala | Pro | Ala | Thr | Leu | Lys | Gly | Glu | Thr | His | Arg | | 348 |
| 1055 | CTG | GAC | TTT | CTG | GCT | CCA | GCC | ACC | CTA | AAA | GGG | GAG | ACA | CAC | CGC | | 1102 |
| 349 | Leu | Phe | Pro | Asn | Thr | Met | Ser | Ala | Phe | Leu | Ser | Glu | Gly | Val | Gly | Ser | 364 |
| 1103 | CTG | TTC | CCC | AAC | ACC | ATG | AGT | GCC | TTT | CTC | TCA | GAG | GGG | GTG | GGC | TCC | 1150 |
| 365 | Lys | Phe | Glu | Gln | Ser | Val | Arg | Leu | Gly | Ser | Trp | Asp | Arg | Gly | Met | 380 |
| 1151 | AAG | TTC | GAG | CAG | AGT | GTG | CGG | CTA | GGC | TCC | TGG | GAT | CGA | GGG | ATG | 1198 |
| 381 | Gln | Tyr | Ser | His | Ser | Ile | Ile | Thr | Asn | Leu | Leu | Tyr | His | Val | Val | Gly | 396 |
| 1199 | CAG | TAC | AGC | CAC | AGC | ATC | ATC | ACG | AAC | CTC | CTG | TAC | CAT | GTG | GTC | GGC | 1246 |
| 397 | Trp | Thr | Asp | Trp | Asn | Leu | Ala | Leu | Asn | Pro | Glu | Gly | Gly | Pro | Asn | Trp | 412 |
| 1247 | TGG | ACC | GAC | TGG | AAC | CTT | GCC | CTG | AAC | CCC | GAA | GGA | GGA | CCC | AAT | TGG | 1294 |
| 413 | Val | Arg | Asn | Phe | Val | Asp | Ser | Pro | Ile | Ile | Val | Asp | Ile | Thr | Lys | Asp | 428 |
| 1295 | GTG | CGT | AAC | TTT | GTC | GAC | AGT | CCC | ATC | ATT | GTA | GAC | ATC | ACC | AAG | GAC | 1342 |

FIG. 1-C

| 429 1343 | Thr ACG | Phe TTT | Tyr TAC | Lys AAA | Gln CAG | Pro CCC | Met ATG | Phe TTC | Tyr TAC | His CAC | Leu CTT | Gly GGC | His CAC | Phe TTC | Ser AGC | Lys AAG | 444 1390 |
| 445 1391 | Phe TTC | Ile ATT | Pro CCT | Glu GAG | Gly GGC | Ser TCC | Gln CAG | Arg AGA | Val GTG | Gly GGG | Leu CTG | Val GTT | Ala GCC | Ser AGT | Gln CAG | Lys AAG | 460 1438 |
| 461 1439 | Asn AAC | Asp GAC | Leu CTG | Asp GAC | Ala GCA | Val GTG | Ala GCA | Leu TTG | Met ATG | His CAT | Pro CCC | Asp GAT | Gly GGC | Ser TCT | Ala GCT | Val GTT | 476 1486 |
| 477 1487 | Val GTG | Val GTC | Leu CTA | Asn AAC | Arg CGC | Ser TCC | Lys AAG | Asp GAT | Val GTG | Pro CCT | Leu CTT | Thr ACC | Ile ATC | Lys AAG | | | 492 1534 |
| 493 1535 | Asp GAT | Pro CCT | Ala GCT | Val GTG | Gly GGC | Phe TTC | Leu CTG | Glu GAG | Thr ACA | Ile ATC | Ser TCA | Pro CCT | Gly GGC | Tyr TAC | Ser TCC | Ile ATT | 508 1582 |
| 509 1583 | His CAC | Thr ACC | Tyr TAC | Leu CTG | Trp TGG | Arg CGT | Arg CGC | Gln CAG | CAG | TGA | TGG | AGC | AGA | TAC | TCA | AGG | AGG | 1630 |
| 1631 | CAC | TGG | GCT | CAG | CCT | GGG | CAT | TAA | AGG | GAC | A | | | | | | |

FIG. 1-D

CLONED DNA FOR SYNTHESIZING UNIQUE GLUCOCEREBROSIDASE

This application is a continuation, of application now abandoned, Ser. No. 07/925,333, filed Aug. 6, 1992, which is a continuation of Ser. No. 07/474,307, filed Feb. 5, 1990, now abandoned, which is a continuation of Ser. No. 07/137.796, filed Dec. 23, 1987, now abandoned.

BACKGROUND OF THE INVENTION

1. Technical Field

The present invention is related to the construction of an expression vector for the synthesis of a recombinant enzyme. More particularly, the present invention is related to the large scale production of glucocerebrosidase by infecting invertebrate cells with a recombinant baculovirus containing the complete cDNA sequence for encoding glucocerebrosidase.

2. State of the Art

Mutation or deficiency of the lysosomal glycoprotein glucocerebrosidase (EC 3.2.1.45, β-D-glucosyl-N-acylsphingosine glycohydrolase) results in Gaucher's disease. It is estimated that there are about 20,000 cases of this genetic disease in the U.S. alone.

Published methods for producing large quantities of the active human enzyme involve purification of the protein from large amounts of human tissue, such as placenta. It should be noted, however, that the placental glucocerebrosidase has carbohydrate structure different than that of the enzyme found in human liver, spleen, brain or macrophages.

Construction of a cDNA clone containing the entire human glucocerebrosidase coding region has been known (Sorge et al, *Proc. Natl. Acad. Sci. USA* 82:7289–7293, 1985). However, as it will become clear vide infra, both the cDNA clone of the present invention and the enzyme synthesized therefrom, are qualitatively different from the similar prior art entities.

SUMMARY OF THE INVENTION

It is, therefore, an object of the present invention to provide a means of cloning human cDNA containing the complete coding region for the lysosomal glycoprotein glucocerebrosidase (GCS), and introducing such sequences into suitable vector systems. A preferred means disclosed introduces the cDNA into *Autographa californica* nuclear polyhedrosis virus downstream to the polyhedrin promoter.

It is a further object of the present invention to provide synthetic, isolated and substantially pure recombinant GCS in which the carbohydrate moiety in the glycoprotein structure is different from the human placental GCS.

It is another object of the present invention to provide a method for large scale production of recombinant GCS by infecting *Spodoptera frugiperda* cells with the recombinant vector of the present invention.

It is a still further object of the present invention to provide a method for treating Gaucher's disease comprising administering to a subject inflicted with Gaucher's disease, a therapeutic amount of the recombinant GCS to alleviate the disease condition.

Other objects and advantages of the present invention will become apparent from the following Detailed Description of the Invention.

BRIEF DESCRIPTION OF THE DRAWINGS

FIG. 1 shows DNA sequence of a human glucocerebrosidase cDNA which was inserted into the baculovirus derived vector, pAC373/GC. In addition to the nucleotide sequence, the amino acid sequence encoded by the coding sequence of the cDNA for human lysosomal glucocerebrosidase is also shown;

DETAILED DESCRIPTION OF THE INVENTION

The present invention provides biologically active GCS. The advantages of the present invention are achieved by cloning a cDNA containing the complete coding sequence for human lysosomal glucocerebrosidase as shown in FIG. 1, said cDNA being then inserted into the genome of *Autographa californica* nuclear polyhedrosis virus downstream to the polyhedrin promoter as shown schematically in FIG. 2.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "substantially pure" as defined herein means as pure as can be obtained by standard purification techniques known to one of ordinary skill in the art.

Materials and Methods

Materials: Restriction endonucleases and recombinant enzymes were obtained from either Life Science Technologies or New England Biolabs. Concanavalin A-Sepharose was obtained from Pharmacia. Octyl-Agarose and Decyl-Agarose were purchased from ICN Biomedicals, Inc. Polyvinylidene difluoride (PVDF) membranes, 0.45 µm pore size, were obtained from Millipore Corp. Sequencer chemicals and solvents for on-line PTH analysis were purchased from Applied Biosystems Inc. Endoglycosidase H was from Miles Scientific while N-Glycanase was purchased from Genzyme Corp.

Figure 2:
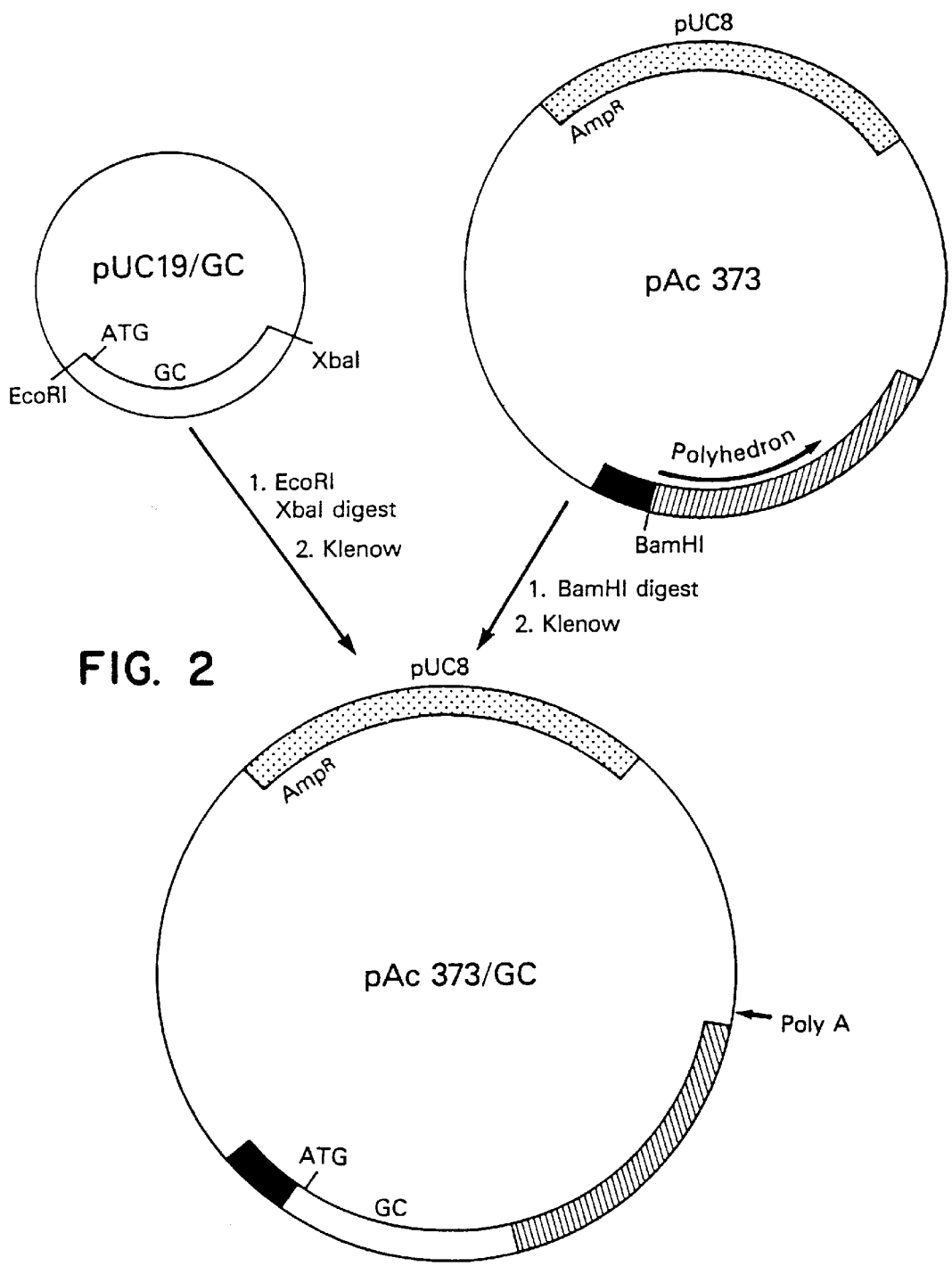
FIG. 2 shows schematic construction of baculovirus derived vector containing a cDNA which encodes human glucocerebrosidase. The cDNA for human glucocerebrosidase containing the sequence shown in FIG. 1 was blunted and then ligated into the SmaI site of a pUC vector (for instance pUC19) yielding pUC19/GC with the cDNA for human glucocerebrosidase lying between unique EcoRI and XbaI sites. The human glucocerebrosidase cDNA could be excised with EcoRI and XbaI, blunted, and ligated in a blunted BamHI site in the baculovirus derived vector, pAC373/GC. This baculovirus vector construct, pAC373/GC, contains human glucocerebrosidase cDNA downstream from the polyhedrin promoter in a 5' to 3' orientation.
Figure 3:
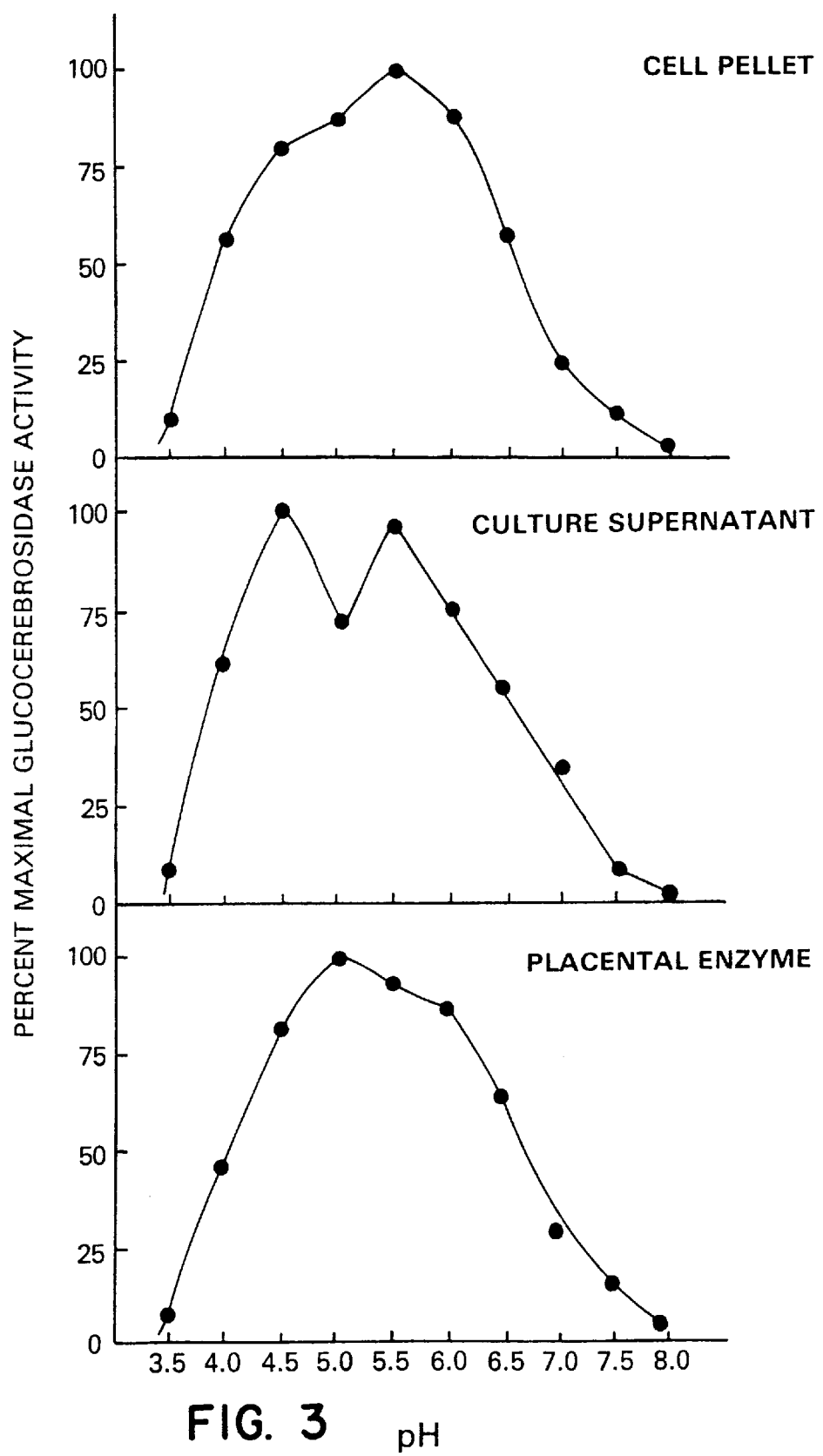
FIG. 3 shows comparative data of pH profiles of human placental glucocerebrosidase and the recombinant enzyme produced by using the baculovirus expression system. The recombinantly produced human glucocerebrosidase in both the cell pellet and the culture supernatant has a broad range of pH activity (between pH 3.5 and pH 8.0) with pH optima at approximately pH 4.5 and pH 5.5. The human placental enzyme has a broad range of pH activity (between pH 3.5 and pH 8.0) with pH optima at approximately pH 5.0 and pH 6.0.

Construction of recombinant Baculoviruses: *Spodoptera frugiperda* SF9 cells, plasmid pAc373, and wild-type AcNPV strain E2 were obtained from Max Summers, Texas A&M University. The SF9 cells were maintained in culture at 28° C. using TNM-FH media (GIBCO) (Hink, *Nature* 226:466, 1970). The cDNA for human glucocerebrosidase was obtained from plasmid pUC19/GC, a derivative of an Okayama-Berg clone from a SV40 transformed human fibroblast cDNA library (Okayama et al, *Mol. Cell Biol.* 3:280, 1983). This cDNA contained 5' and 3' untranslated sequences as well as the complete coding region for glucocerebrosidase. As shown in FIG. 2, pAc373/GC was generated by ligation of the blunted EcoRI-XbaI fragment from pUC19/GC into the blunted unique BamHI site of pAC373. Correct orientation of the inserted glucocerebrosidase cDNA was determined by restriction endonuclease analysis.

Recombinant baculovirus containing the human glucocerebrosidase coding sequence under transcriptional control of the polyhedrin promoter was produced by cotransfection of wild-type virus, AcNPV, with plasmid pAc373/GC into SF9 cells as described by Summers et al, (*Tex. Agric. Exp. Stn. Bull.* No. 1555, 1987). Five to six days after cotransfection, virus was harvested from the culture supernatant and used to inoculate new monolayers of SF9 cells in petri dishes that were subsequently overlaid with 1% low melting agarose containing TNM-FH medium. Seventy-two hours later the agarose overlay was removed and stored at 4° C., and the cell monolayer was blotted onto a nitrocellulose disk (BA85, Schleicher & Schuell). The disk was hybridized to the random primed, $^{32}$p labelled EcoRI-XbaI glucocerebrosidase cDNA fragment from pUC19/GC. Areas on the agarose overlay corresponding to points on the nitrocellulose disk showing hybridization signal were excised and placed in one milliliter of TNM-FH medium. This virus was used for infection of SF9 monolayer cultures and an additional 5 cycles of infection-hybridization were carried out during the plaque purification procedure.

A deposit of PAc373/GC has been made at the ATCC, 12301 Parklawn Dr. Rockville, Ma. on Nov. 30, 1987 under the accession number 40393. The deposit shall be viably maintained, replacing if it became non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

Enzyme purification: Recombinantly produced glucocerebrosidase was isolated using a modification of the procedure described by Furbish et al, (*Proc. Natl. Acad. Sci. USA* 74:3560, 1977). Cell culture supernatants were precipitated with 195 gm/liter ammonium sulfate. SF9 cell pellets containing the recombinantly produced glucocerebrosidase were extracted into 20 milliliters of sodium phosphate buffer, pH 6.5, containing 150 mM NaCl and 0.1% Triton X-100, followed by sonication twice at 50W for 10 seconds. After precipitation with ammonium sulfate (195 gm/liter) the resuspended pellets were extracted with n-butanol, but ultrafiltration using a YM30 membrane (Amicon) replaced dialysis. After decyl-agarose and octyl-agarose hydrophobic interaction chromatography at room temperature (about 22°–25° C.), the fractions containing glucocerebrosidase activity were pooled, and the ethylene glycol concentration reduced using an Amicon ultrafiltration cell fitted with a YM30 membrane.

Substantially pure enzyme is then obtained following standard conventional purification techniques well known in the art.

Carbohydrate characterization. Endoglycosidase-H was dissolved in 100 mM sodium acetate, pH 6.0, at a final concentration of 10 units/ml. N-glycanase was supplied as a 250 unit/ml suspension in 50% glycerol. Either human placental enzyme or fifty microliter aliquot of decyl-agarose fraction containing glucocerebrosidase activity were adjusted to 0.5% NaDodSo$_4$/1M β-mercaptoethanol and boiled for two minutes. The samples were then diluted with appropriate buffer to either 200 mM sodium acetate, pH 6.0 (for endoglycosidase-H) or 200 mM sodium phosphate, pH 8.5 (for N-glycanase) to a final composition of 0.1% SDS, 0.7% NP-40, and 0.02M β-mercaptoethanol. The samples were again boiled for 1 min and then either endoglycosidase-H or N-glycanase added to final concentrations of 50 mu/ml or 20 Ul/ml, respectively. Digestions were for about 16 hours at 37° C. Carboxypeptidase Y was used as a control for both deglycosylation reactions.

Western blot analysis: NaDodSO$_4$ polyacrylamide gel electrophoresis and Western blot analysis were performed as described by Ginns et al, (*Proc. Natl. Acad. Sci. USA* 79:5607, 1982).

Amino acid sequence analysis: Samples used for amino acid sequence analysis were electrophoretically fractionated on NaDodSO$_4$ polyacrylamide gels as described above and then transferred to PVDF membranes as described by Matsudaira (*J.B.C.* 262:10035, 1987). Typically, after electrophoresis the gel was incubated in transfer buffer (0.0M CAPS, 10% methanol, pH 11.0) for 10 minutes prior to transblotting (50 ma for 4 hours). The gel was then washed with HPLC grade water for 5 minutes, stained with 0.1% Coomassie Blue R250 (in 50% methanol) for 5 minutes, and finally destained for 10 minutes with 50% methanol-10% acetic acid. The PVDF membrane was again washed with HPLC grade water, dried under a stream of nitrogen and stored in a sealing bag at −20° C. until used for amino acid sequencing.

Amino acid sequence analysis was accomplished using an Applied Biosystems Model 470A gas-phase sequencer equipped with a Model 120A on-line PTH-amino acid analyzer. The program 03R PTH was used directly for sequencing without pretreatment of the membrane strip with polybrene. An approximately 2×8 mm piece of PVDF membrane containing the protein band of interest was excised, centered on the teflon seal, and placed in the cartridge block of the sequencer. Multiple strips of the PVDF membrane could be stacked in this manner, thus increasing the amount of protein available for sequencing. The initial and repetitive yields for sequencing recombinant glucocerebrosidase were calculated by comparison with the yields obtained after 100 picomoles of human placenta glucocerebrosidase were electrophoresed, transblotted to PVDF and subjected to ten cycles of amino acid sequence (Table 1).

Table 1 compares the N-terminal amino acid sequence of mature human placental glucocerebrosidase to N-terminal amino acid sequence of recombinant human glucocerebrosidase using the methods described in the text. The N-terminal amino acids determined by direct chemical sequencing of the mature human placental and recombinant glucocerebrosidase are identical indicating that the signal sequence in the recombinantly produced enzymes are correctly processed. The blank in amino acid position 4 of the recombinant enzyme sequence is consistent with cysteine because cysteine was only identified in the placental enzyme following reduction and alkylation of the protein. The vertical arrow above the human cDNA sequence indicates the site of peptidase cleavage of the signal sequence.

limited to AIDS virus and hepatitis virus). The recombinantly produced glucocerebrosidase is not associated with these potential complications.

Figure 4:
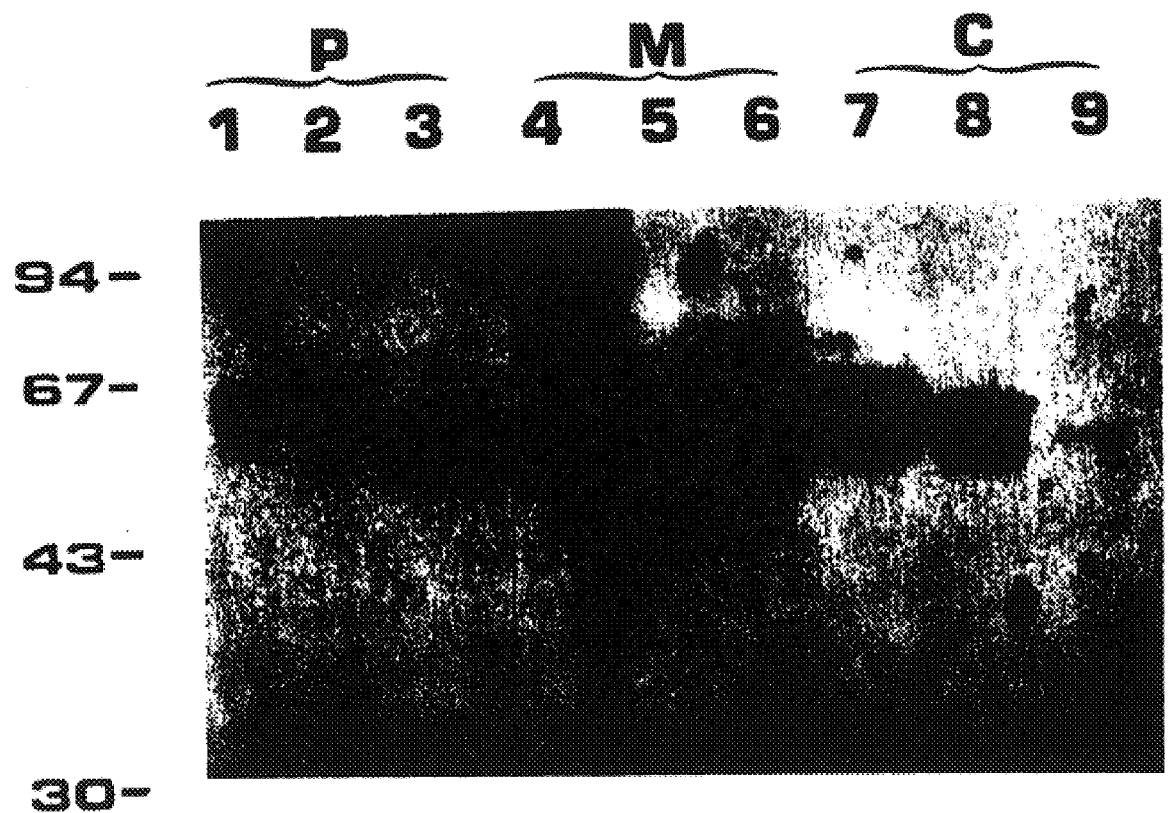
FIG. 4 presents comparative results by Western blot analysis of human placental glucocerebrosidase and the recombinant human glucocerebrosidase produced in the a eucaryotic SF9 cells. Sample preparation, electrophoresis and Western blot analysis were performed as described in the text. Molecular weight size markers (Mr $X10^{-3}$) were phosphorylase b, albumin, ovalbumin, and carbonic anhydrase. P, placental enzyme; M, media glucocerebrosidase; and C, cell-associated glucocerebrosidase. Western blot from untreated placental enzyme and recombinantly produced protein are shown in lanes P1 and, M4 and C7, respectively. Cross reactive material (CRM) from endoglycosidase-H and N-glycanase digested samples are shown in lanes P2, M5, C8, and P3, M6, C9, respectively.

(4) The carbohydrate structure of glucocerebrosidase isolated from human placenta is different from that of recombinantly produced glucocerebrosidase by the baculovirus system (see FIG. 4).

TABLE 1

|     |     |     |       |     | ↓   |     |     |     |     |     |     |     |     |     |                   |
|-----|-----|-----|-------|-----|-----|-----|-----|-----|-----|-----|-----|-----|-----|-----|-------------------|
| ATG | GCT | GGC | ......TCA | GGT | GCC | CGC | CCC | TGC | ATC | CCT | AAA | AGC | TTC | GGC | :cDNA             |
| M   | A   | G   |       | S   | G   | A   | R   | P   | C   | I   | P   | K   | S   | F   | G                 |
|     |     |     |       |     |     | A   | R   | P   | C   | I   | P   | K   | S   | F   | G  :placental enzyme |
|     |     |     |       |     |     | A   | R   | P   | -   |     |     |     |     |     | :culture media    |
| I   | P   | K   | S     | F   | G   |     |     |     |     |     |     |     |     |     |                   |
|     |     |     |       |     |     | A   | R   | P   | -   |     |     |     |     |     | :SF9 cell pellet  |
| I   | P   | K   | S     | F   | G   |     |     |     |     |     |     |     |     |     |                   |

Glucocerebrosidase assays: For pH profile and inhibition studies, glucocerebrosidase activity was measured using 100 mM potassium phosphate buffer containing 0.15% Triton X-100, 2.5 μl of β-D-[1-$^{14}$C] glucocerebroside (7.5 mg/ml in sodium taurocholate at 50 mg/ml), and the sample in the total volume of 200 ul. Preincubations with conduritol-B-epoxide were for 30 min at 37° C. For Km determination, β-glucosidase activity was assayed at pH 5.9 using the artificial substrate 4-methylumbellifery-β-D-glucopyranoside (4MUGP) in 100 mM potassium phosphate buffer containing 0.15% Triton X-100 and 0.125% sodium taurocholate. Purification of recombinant glucocerebrosidase was also monitored using 4MUGP.

FIGS. 1–4 and Table 1 show the comparative results demonstrating the distinctive nature and properties of the cDNA clone and GCS of the present invention relative to the other known similar clones and enzymes, particularly comparing the Sorge et al clone and placenta enzyme.

The distinctive properties are listed below:
(1) The human cDNA of the present invention for glucocerebrosidase differs in both nucleotide sequence and translated amino acid sequence from that of Sorge et al (PNAS, 1985, and Correction PNAS, 1986). Specifically, the cDNA of the present invention encodes for Leu (at 489) and Arg (at 514) while that of Sorge et al, encodes Pro and His at position 489 and 514, respectively. In addition, this cDNA sequence differs in three nucleotides from that reported by Tsuji et al, (J.B.C. 261:50, 1986).
(2) The high level baculovirus expression system differs from other expression systems as should be known to those familar with the subject. For example, the proteins expressed using bacterial hosts do not have the carbohydrate moieties that are added by eukaryotic hosts. Transient expression systems utilizing COS cells or L cells produce only about 200,000 Units glucocerebrosidase/liter (Choudary et al, 1986) while the baculovirus expression system produces over 2,400,000 units glucocerebrosidase/liter after three days of culture. Similarly, enzyme produced in heterologous cells following retroviral gene transfer produces approximately 200,000 units glucocerebrosidase/liter (Choudary et al, 1986, Cold Spring Harbor Symposia, Vol LI: 1047).
(3) The purification of human glucocerebrosidase from large amounts of human placenta must take into account the risk of the possible presence of infectious agents (such as but not (5) Several biochemical parameters of the human placental enzyme are different than that of the recombinant glucocerebrosidase produced by employing the baculovirus expression system:

1) The human placental enzyme on Western blot analysis showed a major band of cross reactive material (CRM) at 65 kDa (see FIG. 4), while the recombinantly produced enzyme has multiple CRM forms between 67 and 52 kDa. However, upon enzymatic removal of carbohydrate, both the recombinantly produced and placental enzyme has a single major CRM form at 52 kDa.

2) The recombinant enzyme was active between pH 3.5 and pH 8.0 with pH optima at pH 4.5 and pH 5.5. The human placental enzyme was active between pH 3.5 and pH 8.0 with pH optima at pH 5.0 and pH 6.0 (see FIG. 3).

3) The recombinantly produced enzyme in the media and cell pellet have Km's of 3.3 mM and 3.6 mM. respectively. The Km for the placental enzyme is reported to be 8 mM (Basu et al, J.B.C. 259:1714, 1984).

It is clear from the above that the recombinantly produced GCS of the present invention is a qualitatively different protein than any other heretofore known entity.

Since the carbohydrate pattern of the recombinantly produced GCS of the present invention is more like that of the human liver, spleen, brain or macrophage GCS, as compared to the placental enzyme and obtained in large quantities by the expression vector of the present invention, replacement therapy of Gaucher's disease now becomes possible for treating patients afflicted with this disease. A method of treating this disease comprises administering to a subject afflicted with Gaucher's disease, therapeutic amounts of recombinant GCS of the present invention to alleviate said disease condition.

A pharmaceutical composition comprises therapeutic amounts of the GCS of the present invention and pharmaceutically acceptable carrier such as physiological saline, non-toxic sterile buffers and the like.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A *Spodoptera frugiperda* insect cell infected by a recombinant baculovirus vector, said vector containing as an insert a polynucleotide consisting of a nucleotide sequence encoding the amino acid sequence of the protein shown in FIG. 1.

2. The insect cell according to claim 1, wherein said insect cell is *Spodoptera frugiperda* SF9.

3. The insect cell according to claim 1, wherein said recombinant baculovirus vector is derived from baculovirus *Autographa californica* AcNPV.

4. A recombinant baculovirus vector containing as an insert the polynucleotide encoding the amino acid sequence of the protein shown in FIG. 1.

5. A pAc373/GC plasmid having ATCC Accession Number 40393.

6. A *Spodoptera frugiperda* insect cell contransfected with a wild type baculovirus and the pAc 373/GC plasmid containing as an inset the cDNA for human glucocerebrosidase.

7. Glycosylated glucocerebrosidase produced by a process comprising the steps of:
   a) cotransfecting a *Spodoptera frugiperda* insect cell with a wild type baculovirus and a pAc373/GC plasmid containing as an insert the cDNA for human glucocerebrosidase under conditions such that a recombinant baculovirus is formed containing as an insert a human glucocerebrosidase coding sequence under transcriptional control of a polyhedrin promotor;
   b) isolating said recombinant baculovirus;
   c) introducing said expression vector into a *Spodoptera frugiperda* insect cell under conditions such that said coding sequence is expressed and glucocerebrosidase is thereby produced; and
   d) isolating said glycosylated glucocerebrosidase.

8. The glycosylated glucocerebrosidase according to claim 7, wherein said insect cell of part c) is a *Spodoptera frugiperda* SF9 insect cell.

9. A glycosylated glucocerebrosidase according to claim 7, wherein said baculovirus comprises wildtype baculovirus AcNPV.

10. A method of producing, glycosylated enzymatically active human glucocerebrosidase, comprising the steps of:
    a) constructing a recombinant baculovirus expression vector containing as an insert a polynucleotide encoding the amino acid sequence of the human glucocerebrosidase shown in FIG. 1;
    b) introducing said expression vector into a *Spodoptera frugiperda* insect cell under conditions such that said insect cell is transformed;
    c) culturing said transformed insect cell in a culture medium under conditions such that said polynucleotide is expressed and glycosylated, enzymatically active glucocerebrosidase is produced; and,
    d) isolating said glucocerebrosidase.

11. A method according to claim 10, wherein said baculovirus vector is derived from the *Autographa californica* nuclear polyhedrosis virus.

12. A method according to claim 10, wherein said insect cell is a *Spodoptera frugiperda* SF9 insect cell.

13. Glycosylated, enzymatically active human glucocerebrosidase produced by a process comprising the steps of:
    a) constructing a recombinant baculovirus expression vector containing as an insert a polynucleotide encoding the sequence of amino acids of the human glucocerebrosidase shown in FIG. 1;
    b) introducing said expression vector into a *Spodoptera frugiperda* insect cell under conditions such that said insect cell is transformed; and,
    c) culturing said transformed insect cell in a culture medium under conditions such that said polynucleotide is expressed, and mature, glycosylated, enzymatically active glucocerebrosidase is produced.

14. The glucocerebrosidase according to claim 13, wherein said baculovirus vector is derived from the *Autographa californica* nuclear polyhedrosis virus.

15. The glucocerebrosidase according to claim 13, wherein said insect cell is a *Spodoptera frugiperda* SF9 insect cell.

* * * * *